(12) United States Patent
Ramos et al.

(10) Patent No.: US 12,102,491 B2
(45) Date of Patent: Oct. 1, 2024

(54) BIOPSY MARKER

(71) Applicant: Devicor Medical Products, Inc., Cincinnati, OH (US)

(72) Inventors: Ramon Alberto Ramos, Loveland, OH (US); Jessica Pyzoha Leimbach, Cincinnati, OH (US); Andrew Thomas Robinson, Cincinnati, OH (US); Gwendolyn Perez Payne, Cincinnati, OH (US); Bryan Robert Keller, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 384 days.

(21) Appl. No.: 17/409,879

(22) Filed: Aug. 24, 2021

(65) Prior Publication Data

US 2022/0008160 A1    Jan. 13, 2022

Related U.S. Application Data

(60) Continuation of application No. 16/668,610, filed on Oct. 30, 2019, now Pat. No. 11,123,151, which is a division of application No. 15/478,929, filed on Apr. 4, 2017, now Pat. No. 10,492,884, which is a
(Continued)

(51) Int. Cl.
*A61B 90/00* (2016.01)
*A61B 10/02* (2006.01)
*A61B 17/00* (2006.01)

(52) U.S. Cl.
CPC .......... *A61B 90/39* (2016.02); *A61B 10/0275* (2013.01); *A61B 2017/00004* (2013.01); *A61B 2017/0088* (2013.01); *A61B 2017/00898* (2013.01); *A61B 2090/3908* (2016.02); *A61B 2090/3912* (2016.02); *A61B 2090/3925* (2016.02); *A61B 2090/3954* (2016.02); *A61B 2090/3966* (2016.02); *A61B 2090/3987* (2016.02); *A61B 2090/3991* (2016.02); *A61B 2090/3995* (2016.02)

(58) Field of Classification Search
CPC ............................ A61B 10/0275; A61B 90/39
USPC ........................................................ 600/567
See application file for complete search history.

(56) References Cited

U.S. PATENT DOCUMENTS

| | | | |
|---|---|---|---|
| 2007/0149893 A1* | 6/2007 | Heske | A61B 10/0275 600/568 |
| 2008/0188768 A1* | 8/2008 | Zarins | A61B 90/39 600/567 |

(Continued)

*Primary Examiner* — Nicole F Lavert
(74) *Attorney, Agent, or Firm* — Frost Brown Todd LLP

(57) ABSTRACT

A biopsy marker may include three shaped portions arranged sequentially along an axis, each shaped portion having a first surface and a second surface parallel to the first surface. A first narrow portion connects a first of the three shaped portions to a second of the three shaped portions. A second narrow portion connects the second of the three shaped portions to a third of the three shaped portions. The first narrow portion is twisted about the axis such that the first surface of the first shaped portion is at a first angle to the first surface of the second shaped portion. The second narrow portion is twisted about the axis such that the first surface of the second shaped portion is at a second angle to the first surface of the third shaped portion.

18 Claims, 19 Drawing Sheets

Related U.S. Application Data continuation of application No. PCT/US2015/054679, filed on Oct. 8, 2015.

(60) Provisional application No. 62/061,586, filed on Oct. 8, 2014.

(56) References Cited

U.S. PATENT DOCUMENTS

| | | | |
|---|---|---|---|
| 2009/0062872 A1* | 3/2009 | Chin | A61B 1/00082 606/86 R |
| 2011/0071431 A1* | 3/2011 | Speeg | A61B 90/39 600/567 |
| 2011/0218433 A1* | 9/2011 | Speeg | A61B 10/02 600/432 |
| 2015/0025414 A1* | 1/2015 | Rhad | A61B 17/3421 600/567 |

* cited by examiner

FIG. 6
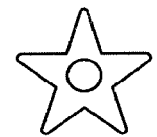
FIG. 7
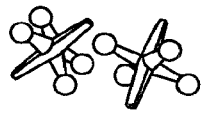
FIG. 8
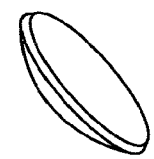
FIG. 9
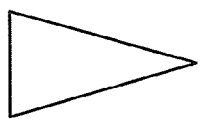
FIG. 10
FIG. 11
FIG. 12
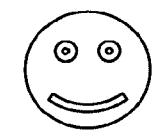
FIG. 13
A
FIG. 14
1
FIG. 15
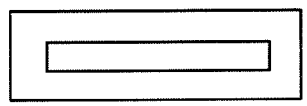
FIG. 16
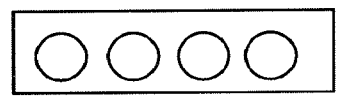
FIG. 17
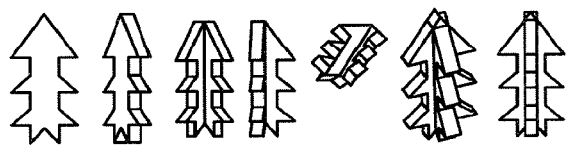
FIG. 18

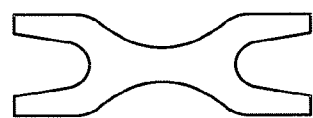 
FIG. 46A  FIG. 46B
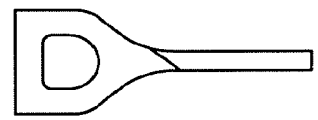 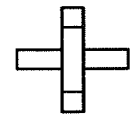
FIG. 47A  FIG. 47B
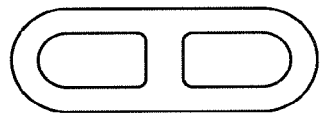 
FIG. 48A  FIG. 48B
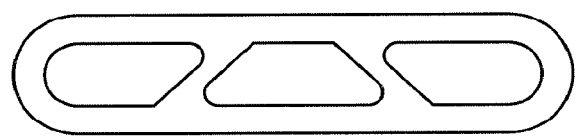 
FIG. 49A  FIG. 49B

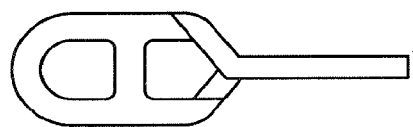 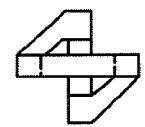
FIG. 50A                FIG. 50B
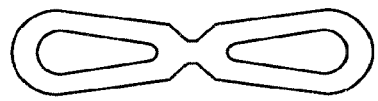 
FIG. 51A                FIG. 51B
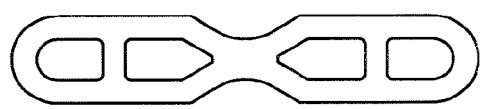 
FIG. 52A                FIG. 52B

BIOPSY MARKER

PRIORITY

This application is continuation of U.S. application Ser. No. 16/668,610 titled "BIOPSY MARKER" filed Oct. 30, 2019, which is a divisional of U.S. application Ser. No. 15/478,929 titled "BIOPSY MARKER" filed Apr. 4, 2017, which is a continuation of International Application Number PCT/US2015/054679 filed Oct. 8, 2015, which claims priority to U.S. Provisional Application No. 62/061,586 titled "BIOPSY MARKER" filed Oct. 8, 2014, all of which are assigned to the assignee of the current application and hereby incorporated herein by reference in their entirety.

BACKGROUND

The disclosure relates to biopsy markers for marking the site of a biopsy. In particular, the disclosure relates to biopsy markers for use in breast biopsy.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

The disclosure provides a biopsy marker. The biopsy marker may include three shaped portions arranged sequentially along an axis, each shaped portion having a first surface and a second surface parallel to the first surface. A first narrow portion may connect a first of the three shaped portions to a second of the three shaped portions. A second narrow portion may connect the second of the three shaped portions to a third of the three shaped portions. The first narrow portion is twisted about the axis such that the first surface of the first shaped portion is at a first angle to the first surface of the second shaped portion. The second narrow portion is twisted about the axis such that the first surface of the second shaped portion is at a second angle to the first surface of the third shaped portion.

The one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements, and in which:

FIGS. 6-18 illustrate various shapes of biopsy markers.
FIGS. 46A and 46B illustrate a flat marker having two shaped portions and a narrow portion.
FIGS. 47A and 47B illustrate a twisted marker having two shaped portions and a narrow portion
FIGS. 48A and 48B illustrate a flat marker having through holes.
FIGS. 49A and 49B illustrate a flat marker having three through holes.
FIGS. 50A and 50B illustrate a twisted marker without a narrow portion.
FIGS. 51A and 51B illustrate a flat marker having two shaped portions and a narrow portion.
FIGS. 52A and 52B illustrate a flat marker having two shaped portions and a narrow portion.

DETAILED DESCRIPTION

Various aspects are now described with reference to the drawings. In the following description, for purposes of explanation, numerous specific details are set forth in order to provide a thorough understanding of one or more aspects. It may be evident, however, that such aspects may be practiced without these specific details.

Figure 1:
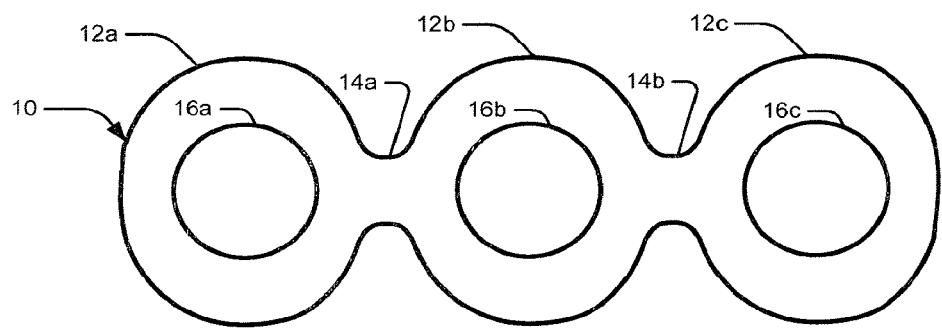
FIG. 1 is a plan view of a flat biopsy marker.

FIG. 1 is a plan view of a flat biopsy marker 10. The flat biopsy marker 10 may include three shaped portions 12a, 12b, 12c. As illustrated, the shaped portions 12a, 12b, 12c are generally circular shaped. However, it should be appreciated that the shaped portions 12a, 12b, 12c may be triangular, rectangular, ellipsoidal, or any other polygonal or curved shapes. In an aspect, the shaped portions 12a, 12b, 12c, may have rounded corners. The shaped portions 12a and 12b may be connected by a narrow portion 14a, and the shaped portions 12b and 12c may be connected by a narrow portion 14b. The shaped portions 12a, 12b, 12c, may be relatively large compared to the narrow portions 14a, 14b. In an aspect, each shaped portion 12a, 12b, 12c may include a respective through hole 16a, 16b, 16c. As illustrated, the through holes 16a, 16b, 16c may be generally circular. However, it should be appreciated that the through holes 16a, 16b, 16c may be triangular, rectangular, ellipsoidal, or any other polygonal or curved shapes. Further, some shaped portions may not have a through hole. For example, the marker 10 may include 1, 2, or 3 shaped portions 12a, 12b, 12c including a through hole 16. In an aspect, the length of the flat biopsy marker 10 may be approximately 2.5 mm. The width at a shaped portion 10 may be approximately 0.76 mm. The blank 10 may be approximately 0.1 mm thick.

In an aspect, the flat biopsy marker 10 may be made from a stainless steel, titanium, or other metallic sheet using a stamping process. A die may be used to cut one or more flat biopsy markers 10 from the sheet. The flat biopsy marker 10 may serve as a blank for a twisted biopsy marker.

Figure 2A:
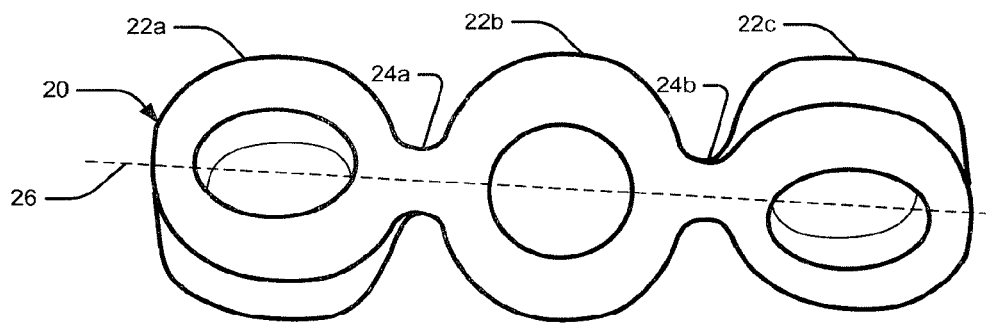
FIG. 2A is a plan view of a twisted biopsy marker.
Figure 2B:
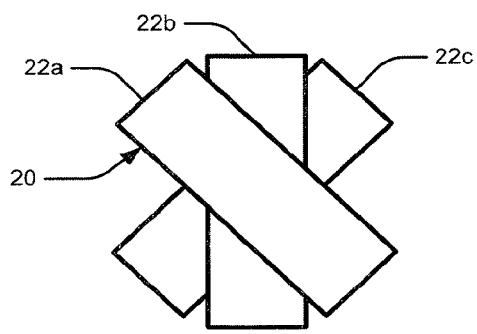
FIG. 2B is an end view of the twisted biopsy marker of FIG. 2A.

FIG. 2A is a plan view of a twisted biopsy marker 20. The twisted biopsy marker 20 may be formed from the flat biopsy marker 10 by twisting the flat biopsy marker 10 at the narrow portions 14a and 14b about an axis 26. Accordingly, the twisted biopsy marker 20 may include three shaped portions 22a, 22b, 22c corresponding to the shaped portions 12a, 12b, 12c. In an aspect, as illustrated in FIG. 2B, the narrow portion 24a may be twisted about the axis 26 such that a first angle between a surface of the shaped portion 22a and a surface of the shaped portion 22b may be approximately 45 degrees. As used herein, the term "approximately," when applied to an angle, may allow a range of plus or minus 5 degrees, for example, to account for manufacturing tolerances. The narrow portion may also be twisted to other angles between 0 degrees and 180 degrees. For example, the narrow portion may be twisted to 15 degrees, 30 degrees, 40 degrees, 50 degrees, 60 degrees, 75 degrees, 90 degrees, etc. In an aspect, the narrow portion 24b may be twisted such that a second angle between the shaped portion 22b and the shaped portion 22c may be approximately 45 degrees, or another angle that differentiates the surface of the shaped portion 22c from the shaped portions 22a and 22b. The second angle may be different than the first angle. In an aspect, the total angle between the shaped portion 22a and the shaped portion 22c may be approximately 90 degrees. Other angles may also be selected, for example, based on imaging techniques to be used to view the marker 20.

Figure 3:
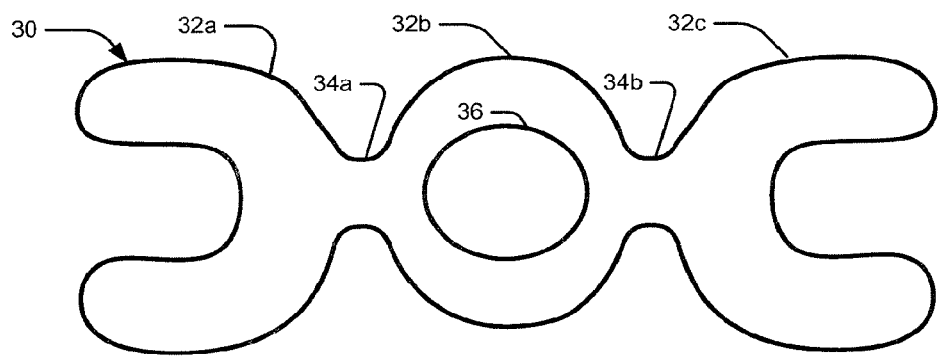
FIG. 3 is a plan view of another flat biopsy marker.

FIG. 3 a plan view of another flat biopsy marker 30. The flat biopsy marker 30 may include three shaped portions 32a, 32b, 32c. As illustrated, the central shaped portion 32b is generally circular shaped. However, it should be appreciated that the shaped portions 32b may be triangular, rectangular, ellipsoidal, or any other polygonal or curved shapes. The central shaped portion 32b may include a through hole 36. As illustrated, the through hole 36 may be generally circular. However, it should be appreciated that the through hole 36 may be triangular, rectangular, ellipsoidal, or any other polygonal or curved shapes. In an aspect, the central shaped portion 32b may not include a through hole, or may include more than one through hole. The end shaped portions 32a and 32c may be an open shape. As illustrated, the end shaped portions 32a and 32c may each be an open semi-circle. The end shaped portions 32a and 32c may each include a respective cut-out 38a, 38b facing the end of the marker blank 30. The shaped portions 32a and 32b may be connected by a narrow portion 34a, and the shaped portions 32b and 32c may be connected by a narrow portion 34b.

Figure 4A:
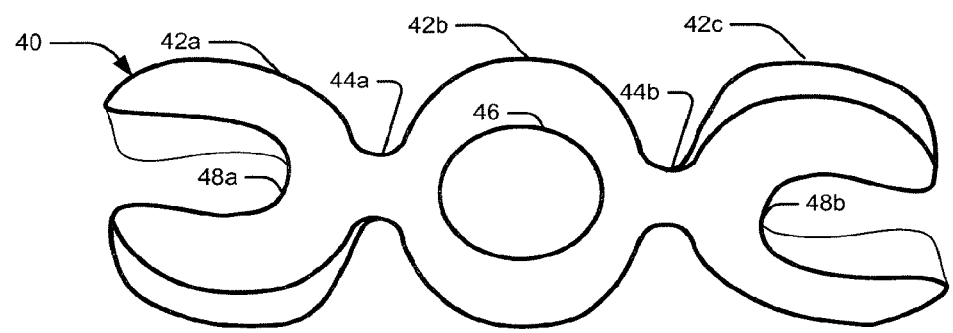
FIG. 4A is a plan view of a twisted biopsy marker.
Figure 4B:
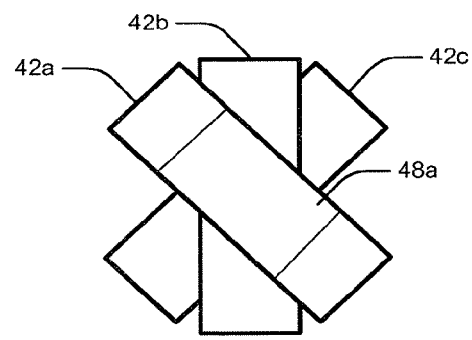
FIG. 4B is an end view of the twisted biopsy marker of FIG. 4A.

FIG. 4A is a plan view of a twisted biopsy marker. The twisted biopsy marker 40 may be formed from the flat biopsy marker 30 by twisting the flat biopsy marker 30 at the narrow portions 34a and 34b. Accordingly, the twisted biopsy marker 40 may include three shaped portions 42a, 42b, 42c corresponding to the shaped portions 32a, 32b, 32c. In an aspect, as illustrated in FIG. 4B, the narrow portion 44a may be twisted such that a first angle between the shaped portion 42a and the shaped portion 42b may be approximately 45 degrees. The narrow portion 34a may be twisted to other angles between 0 degrees and 180 degrees. For example, the narrow portion may be twisted to 15 degrees, 30 degrees, 40 degrees, 50 degrees, 60 degrees, 75 degrees, 90 degrees, etc. In an aspect, the narrow portion 44b may be twisted such that a second angle between the shaped portion 42b and the shaped portion 42c may be approximately 45 degrees, or another angle that differentiates the surface of the shaped portion 42c from the shaped portions 42a and 42b. The total angle between the shaped portion 42a and the shaped portion 42c may be approximately 90 degrees. Other angles may also be selected, for example, based on imaging techniques to be used to view the marker. The cut-outs 48a, 48b may expose a concave surface when the marker 40 is viewed from an end.

In an aspect, the biopsy marker 20 or biopsy marker 40 may be encapsulated in a bioabsorbable material such a collagen, gelatin, etc. The bioabsorbable material may be compressed. In an aspect, the force used to compress the bioabsorbable material may also exert force on the embedded biopsy marker. In an aspect, the size, shape, and thickness of the biopsy marker 20 or biopsy marker 40 may be selected to withstand forces applied during compression without significant deformation or breakage.

In an aspect, the biopsy marker 20 or biopsy marker 40 may be implanted into soft human or animal tissue during a biopsy procedure. For example, the biopsy marker 20, 40 may be inserted into human breast tissue during a breast biopsy to mark the site of the biopsy. If the biopsy marker 20, 40 is embedded within a bioabsorbable material, the bioabsorbable material may help position the biopsy marker 20, 40 within the center of a biopsy cavity. The biopsy marker 20 may rotate within the animal tissue after insertion. Further, when the tissue is being imaged, the tissue may be compressed causing further rotation. The orientation of the biopsy marker may be unknown prior to imaging. The biopsy marker 20 or biopsy marker 40 may be imaged using various imaging techniques including x-ray (stereo), ultrasound, and magnetic resonance imaging (MRI), among other imaging techniques.

Under x-ray, two or more angles may be used to provide a composite stereo image. For example, breast tissue may generally be imaged from a cranial-to-caudal approach, a medial-to-lateral approach, and from a 45 degree angle between the two previous approaches. The twists of the biopsy markers 20, 40 may help increase visibility of the markers 20, 40 from each imaging approach, in addition to helping to identify the markers 20, 40 as having a shape that is recognizable as artificial when compared to the surrounding tissue. For example, if one of the approaches aligns with the longitudinal axis 26 of the biopsy marker 20, 40, the total surface area of the marker may be increased as a partial surface of each of the shaped portions 22, 42 may be imaged.

If the approach is transverse to the longitudinal axis, the surface of at least one of the shaped portions 22, 42 may be imaged.

Under ultrasound, the biopsy markers 20, 40 include various curved and concave surfaces that may provide echogenic features. For example, the through holes 36, 46 may provide echogenic features oriented in different angles. Further, in the biopsy marker 40, the cut-outs 48 may expose a concave surface when the marker 40 is imaged in alignment with the longitudinal axis.

Under MRI, images may be generated using slices in coronal, sagittal, and axial orientations. As discussed above regarding x-ray imaging, the twists of the biopsy markers 20, 40 may provide at least one surface that is visible in each orientation, in addition to helping to identify the markers 20, 40 as having a shape that is recognizable as artificial when compared to the surrounding tissue. Magnetic resonance has further effects based on the material of the marker 20, 40. Metallic materials produce an artifact, that is, an image outside of the physical boundaries of the markers 20, 40. The artifact may also be referred to as a bloom. Generally, the artifact produced by a marker may be a dark spot in an MR image while a lesion or cyst may absorb a contrast agent and produce a relatively bright spot. The artifact produced by a marker may obscure the image of surrounding tissue, making it difficult to determine whether the surrounding tissue includes a lesion or cyst. Some modern MR machines may reduce artifact using advanced image processing techniques. In some cases, such artifact reduction may make it difficult to locate a marker in an image.

Figure 5A:
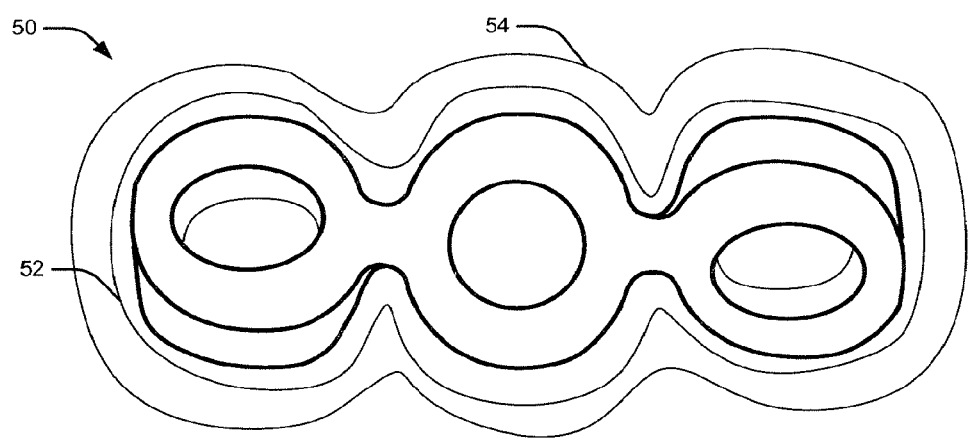
FIGS. 5A and 5B illustrate a representation of the twisted biopsy marker of FIG. 2A under magnetic resonance imaging.
Figure 5B:
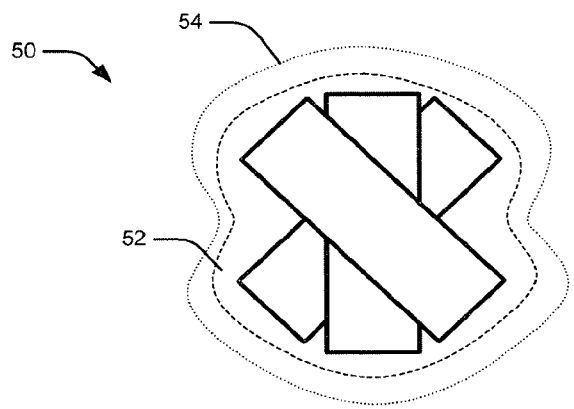

FIGS. 5A and 5B illustrate a representation 50 of the twisted biopsy marker 20 under magnetic resonance imaging. Generally, the artifact produced by a marker is roughly proportional to the mass of the marker. Titanium markers generally produce less artifact than stainless steel markers. For example, the line 52 may illustrate an artifact that may be produced by a titanium marker while the line 54 may illustrate an artifact that may be produced by a stainless steel marker having the same dimensions. Physicians may select a marker based on the MR machine most likely to be used for future imaging of the marker. When imaged transverse to the longitudinal axis, as in FIG. 5A, the twisted biopsy marker 20 may produce three distinct lobes. When imaged along the longitudinal axis, as in FIG. 5B, the twisted biopsy marker 20 may produce a generally circular artifact, but two lobes may be distinguishable. The through holes 16 of the marker 20 or the through hole 46 and cutouts 48 of marker 40 may help reduce the artifact produced by the markers 20, 40. For example, the through holes and cutouts may reduce the mass of each shaped portion in comparison to a similar shaped portion without a through hole or cutout. In an aspect, an artifact may extend into the interior of a through hole or cutout while extending less from the exterior edges of the marker 20, 40.

FIGS. 6-18 illustrate various additional shapes and features for markers. These additional shapes or features may be combined with the twisted markers 20, 40 to create markers having desirable imaging properties. Further, markers of different shapes may be used in subsequent procedures to provide a unique marker for each biopsy location.

FIG. 6 illustrates a star shaped marker.

FIG. 7 illustrates a star shaped marker having a through hole.

FIG. 8 illustrates jack shaped markers. A jack shaped marker may be image-able from different approaches or orientations.

FIG. 9 illustrates a concave dish shaped marker. The concave surface of the marker may provide an echogenic surface under ultrasound imaging.

FIG. 10 illustrates a triangle shaped marker.

FIG. 11 illustrates a cone shaped marker. The cone may be bent to lessen a triangular effect.

FIG. 12 illustrates a heart shaped marker.

FIG. 13 illustrates a marker having a distinct shape formed by through holes. For example, the marker may appear as a smiling face. Different shapes may be created by varying the size and shape of the through holes.

FIG. 14 illustrates a marker shaped like a letter. For example, the marker may be shaped like a capital A. Markers in the shape of different letters or having portions shaped like particular letters may help identify a specific marker.

FIG. 15 illustrates a marker shaped like a number. For example, the marker may be in the shape of the number 1. Markers in the shape of different numbers or having portions shaped like particular numbers may help identify a specific marker.

FIG. 16 illustrates a marker shaped as a rectangle with a through slot.

FIG. 17 illustrates a marker shaped as a rectangle with a pattern of through holes.

FIG. 18 illustrates markers shaped as a barbed arrow. The protrusions or barbs of the marker may provide surfaces that may be imaged from different approaches or orientations.

Figure 19:
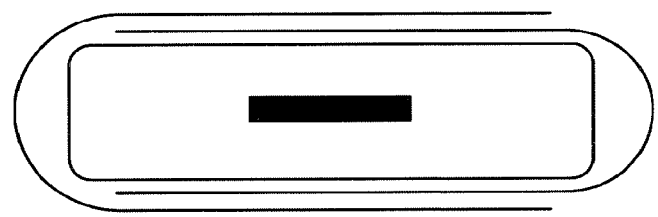
FIG. 19 illustrates a biopsy marker within a capsule.

FIG. 19 illustrates a marker contained in a capsule. The capsule may be formed of a bioabsorbable material such a gelatin that may be absorbed over time at the biopsy cavity. The capsule may include a marker such as the markers 20, 40 discussed above embedded in a second bioabsorbable material. During manufacture, the capsule may have non-uniform features to prevent the two halves from separating. Further, the two capsule halves may be wetted with alcohol or a bonding agent to securely adhere the two halves together.

Figure 20:
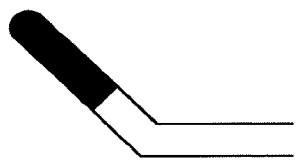
FIGS. 20-22 illustrate a marker and pre-bent push-rod for deploying a marker.
Figure 21:
Figure 22:
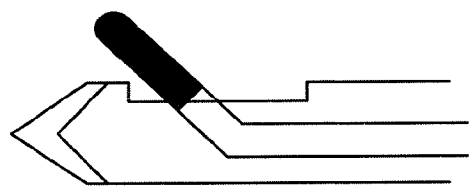

FIG. 20 illustrates a marker and pre-bent push-rod for deploying a marker at a biopsy cavity. The marker may be encapsulated in a bioabsorbable material formed at the end of the pre-bent push-rod. As illustrated in FIG. 21, the marker and pre-bent push rod may be deployed through a biopsy needle. When in the longitudinal cannula of the biopsy needle, the pre-bent push-rod may be straightened. As illustrated in FIG. 22, when the marker reaches the aperture of the biopsy needle, the pre-bent push rod may return to its bent shape and the bioabsorbable material holding the marker may protrude from the biopsy needle. A physician operating the biopsy needle may notice the pre-bent push rod returning to the bent position. The longitudinal movement of the pre-bent push rod may also be prevented when the push-rod returns to the bent configuration. The cutter of the biopsy needle may be used to shear off the tip of the bioabsorbable material including the marker.

Figure 23:
FIG. 23-26 illustrate another marker attached to a pre-bent wire deployer.
Figure 24:
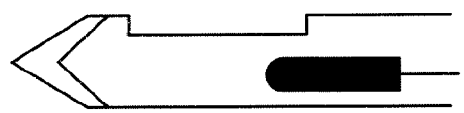
Figure 25:
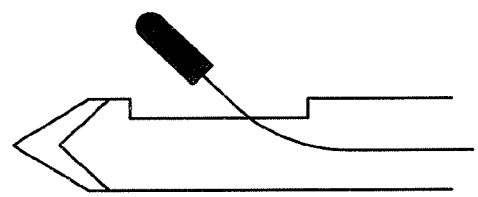
Figure 26:
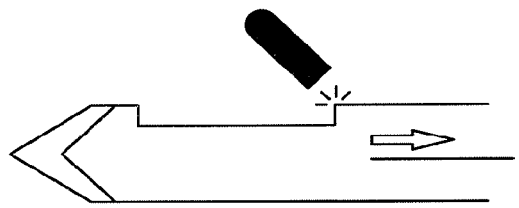

FIG. 23 illustrates another marker attached to a pre-bent wire deployer. The pre-bent wire may be partially embedded in the bioabsorbable material encapsulating the marker. As illustrated in FIG. 24, the marker and pre-bent wire may be deployed through a biopsy needle. When in the longitudinal cannula of the biopsy needle, the pre-bent wire may be straightened. As illustrated in FIG. 25, when the marker reaches the aperture of the biopsy needle, the pre-bent wire may return to its bent shape and the bioabsorbable material holding the marker may protrude from the biopsy needle. A physician operating the biopsy needle may notice the pre-bent wire returning to the bent configuration. The longitudinal movement of the pre-bent wire may also be prevented when the push-rod returns to the bent configuration. When the pre-bent wire is pulled proximally, the bioabsorbable material may catch on the edge of the aperture of the biopsy needle or the cutter, or may otherwise prevent the encapsulated marker from retracting with the wire, thus removing the wire from the bioabsorbable material and leaving the marker at the biopsy cavity.

Figure 27:
FIGS. 27-30 illustrate an elongated bioabsorbable marker.
Figure 28:
Figure 29:
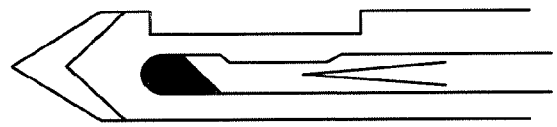
Figure 30:
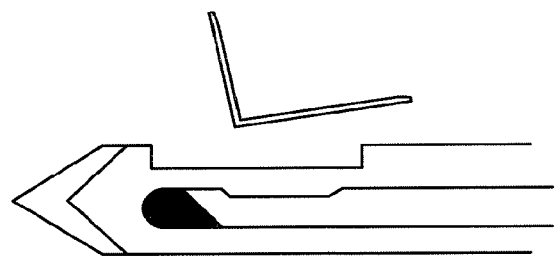

FIG. 27 illustrates an elongated marker formed of a bioabsorbable material such as collagen. One or more permanent metallic or ceramic markers may be embedded in the elongated marker. As illustrated in FIG. 28, the elongated marker may be deployed using a marker deployer. The elongated marker may be bent within the marker deployer. As illustrated in FIG. 29, the marker deployer may be deployed through the cannula of a biopsy needle having a lateral aperture. The elongated marker may be pushed to the distal end of the marker deployer with a push rod. As illustrated in FIG. 30, when the elongated marker is pushed out of the marker deployer, it may straighten. The straightened elongated marker may be unlikely to reenter the aperture of the biopsy needle.

Figure 31:
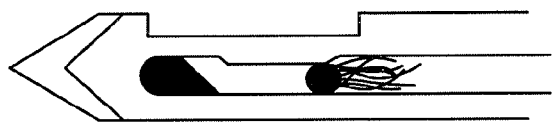
FIGS. 31-32 illustrate a ball shaped marker with tassles.
Figure 32:
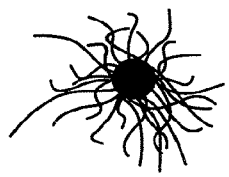
Figure 32:
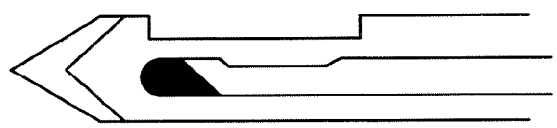

FIG. 31 illustrates a ball shaped marker with tassles. The ball may be made from a bioabsorbable material such as collagen and may include a permanent marker embedded therein. The tassles may be made of a suture material. The ball shaped marker with tassles may be deployed through a marker deployer such that the tassles follow the ball. As illustrated in FIG. 32, once the ball shaped marker with tassles is pushed into the biopsy cavity, the tassles may fan out and help reduce marker migration.

Figure 33:
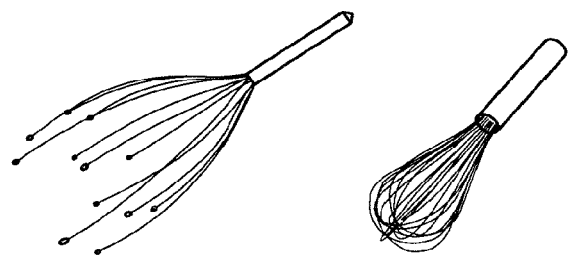
FIG. 33 illustrates a whisk shaped marker.

FIG. 33 illustrates a whisk shaped marker. The tines of the marker may be held together during deployment. Once the marker is deployed, the tines may spread out. The tines may help reduce migration of the marker and may also increase an imagable area of the marker.

Figure 34:
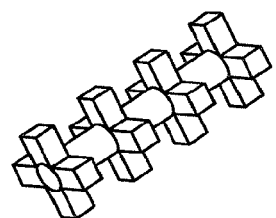
FIG. 34 illustrates a shape for a bioabsorbable material surrounding a marker.

FIG. 34 illustrates a shape for a bioabsorbable material surrounding a marker. The bioabsorbable material may initially be shaped as a cylinder having one or more X shaped sections along the length. The bioabsorbable material may be compressed to fit within a marker deployer. The bioabsorbable material may expand within the biopsy cavity. The X shaped sections may reduce migration and improve imageability. Compared to a cylinder of bioabsorbable material having the same mass, the bioabsorbable material having X shaped sections may have a greater inscribed volume.

Figure 35:
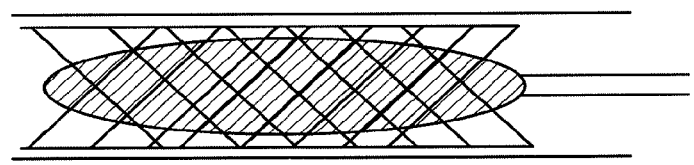
FIGS. 35-37 illustrate a mesh marker.
Figure 36:
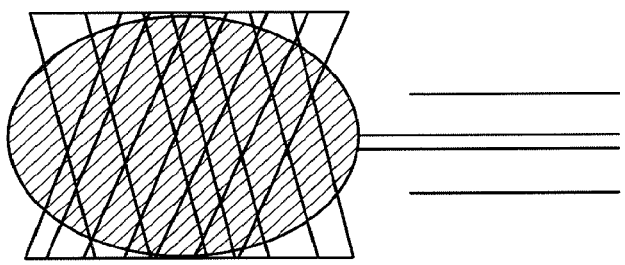
Figure 37:
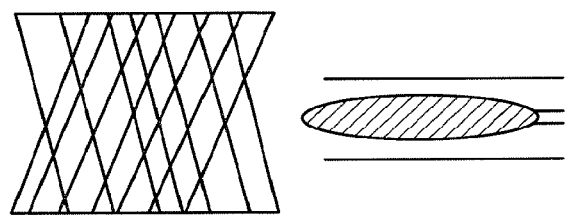

FIG. 35 illustrates a mesh marker inside a deployer. The mesh marker may be deployed using a balloon. As illustrated in FIG. 36, the mesh marker may be deployed past the end of a biopsy needle, and the balloon may be expanded to expand the mesh marker. For example, the mesh marker may be expanded to the size of the biopsy cavity. As illustrated in FIG. 37, the balloon may be deflated and retracted through the biopsy needle, leaving the marker behind.

Figure 38:
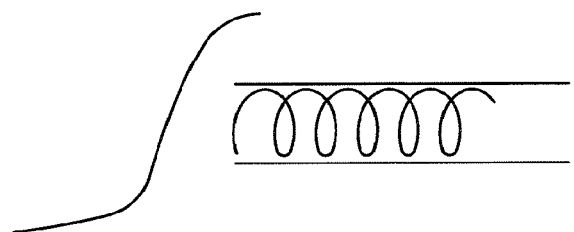
FIGS. 38 and 39 illustrate a helical marker.
Figure 39:
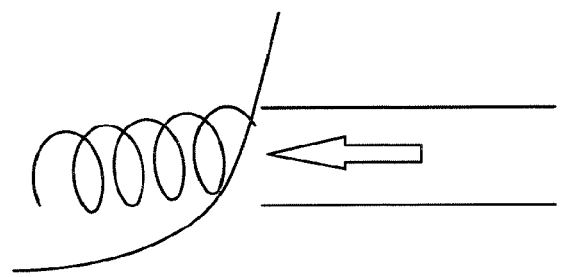

FIG. 38 illustrates a helical marker. The helical marker may be deployed through the distal end of a biopsy needle. As illustrated in FIG. 39, the helical marker may be deployed by screwing the helical marker into tissue at the end of the biopsy needle. The marker deployer may be threaded such that a push-rod rotates as it travels through the deployer. The helical marker may be firmly fixed within the tissue with little likelihood of migration.

Figure 40:
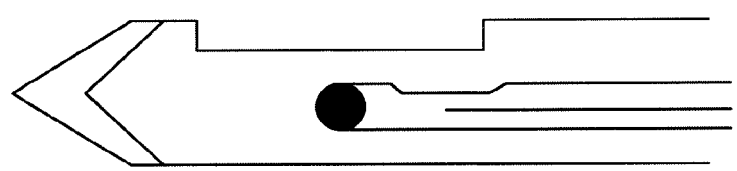
FIGS. 40 and 41 illustrate a coil marker.
Figure 41:
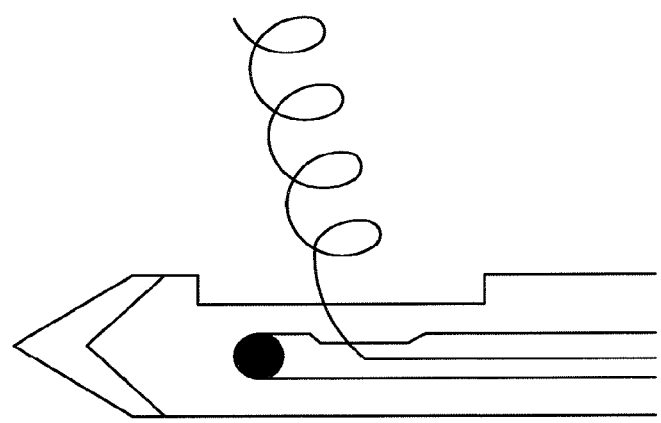

FIG. 40 illustrates a coil marker for deployment through a biopsy needle having a lateral aperture. The coil marker may be a loose spring formed of a material that does not permanently elastically deform when stretched out. For example, the coil marker may be formed of titanium. The coil marker may be straightened for deployment through the longitudinal cannula of a biopsy needle or marker deployer. When the coil marker is deployed into the biopsy cavity, the coil marker may return to the coiled spring configuration as illustrated in FIG. 41.

Figure 42:
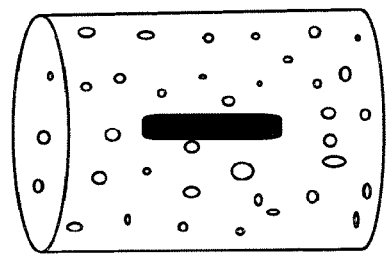
FIG. 42 illustrates a plastic marker with bubbles.

FIG. 42 illustrates a plastic marker with bubbles. The plastic marker may be molded around a metallic or ceramic marker. When the plastic marker is being molded, air bubbles may be induced into the plastic. Bubbles may also be formed using spheres of glass as a filler. The air bubbles or glass spheres may create a density difference in the marker for ultrasound imaging.

Figure 43:
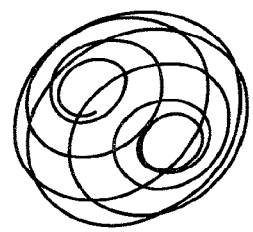
FIG. 43 illustrates a spherical spring marker.

FIG. 43 illustrates a spherical spring marker. The spherical spring marker may be compressed flat and embedded within a bioabsorbable material. The spherical spring marker may be deployed using any of the deployment devices and techniques described herein. The bioabsorbable material may be absorbed at the biopsy cavity and the spherical spring marker may return to a spherical shape.

Figure 44:
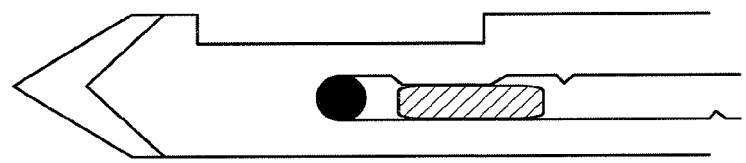
FIGS. 44 and 45 illustrate a crimped marker deployer.
Figure 45:
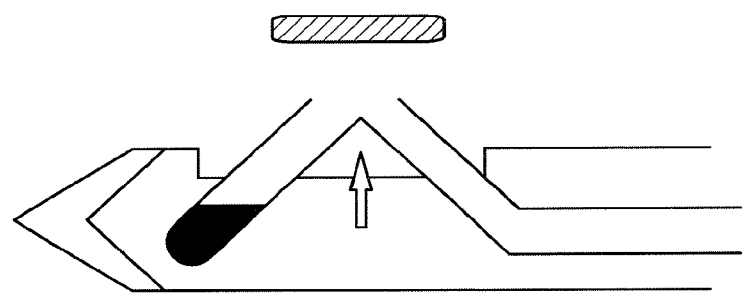

FIG. 44 illustrates a crimped marker deployer. The crimped marker deployer may include crimps, notches, or points of weakness that predetermine how the marker deployer will deform when compressed longitudinally. For example, the crimped marker deployer may include a notch that holds the marker and two crimps proximal to the marker. As illustrated in FIG. 45, when the crimped marker deployer is pushed against the distal end of the biopsy device, the crimped marker deployer may buckle at the notch and the crimps, causing the marker to extend laterally out of a lateral aperture.

FIGS. 46A and 46B illustrate a flat marker having two shaped portions and a narrow portion. Each shaped portion has a cutout on its exterior side. In an aspect, the marker may be approximately 0.1 inches long, 0.037 inches wide and 0.006 inches thick. The dimensions of the marker may vary based on a material of the marker. For example, the dimensions for a titanium marker may be scaled to be larger than a stainless steel marker.

FIGS. 47A and 47B illustrate a twisted marker having two shaped portions and a narrow portion. Each shaped portion has a D-like shape and includes a through hole shaped like the letter D. In an aspect, the marker may be approximately 0.1 inches long, 0.037 inches wide and 0.007 inches thick.

FIGS. 48A and 48B illustrate a flat marker having through holes. In an aspect, the marker may have an elongated oval shape. Each through hole may be shaped like a wide letter D. The marker may be approximately 0.1 inches long, 0.037 inches wide and 0.007 inches thick.

FIGS. 49A and 49B illustrate a flat marker having three through holes. The marker may be an elongated oval shape approximately 0.16 inches long, 0.37 inches wide and 0.007 inches thick. The through holes may be different shapes such as trapezoids. Bridging portions may connect the elongated sides between through holes. The bridging portions may be slanted or straight.

FIGS. 50A and 50B illustrate a twisted marker without a narrow portion. Instead, the twisted marker may be formed from an elongated oval shaped flat marker. When twisted, the elongated sides of the marker may bend. The marker may be approximately 0.12 inches long, 0.037 inches wide and 0.007 inches thick.

FIGS. 51A and 51B illustrate a flat marker having two shaped portions and a narrow portion. The shaped portions may be wider toward the outside and narrow toward the middle. The shaped portions may include through holes of similar shape. In an aspect, the marker may be approximately 0.1 inches long, 0.026 inches wide and 0.007 inches thick.

FIGS. 52A and 52B illustrate a flat marker having two shaped portions and a narrow portion. Each shaped portion may be elongated and include multiple through holes. In an aspect, the marker may be approximately 0.13 inches long, 0.026 inches wide and 0.007 inches thick.

Figure 53A:
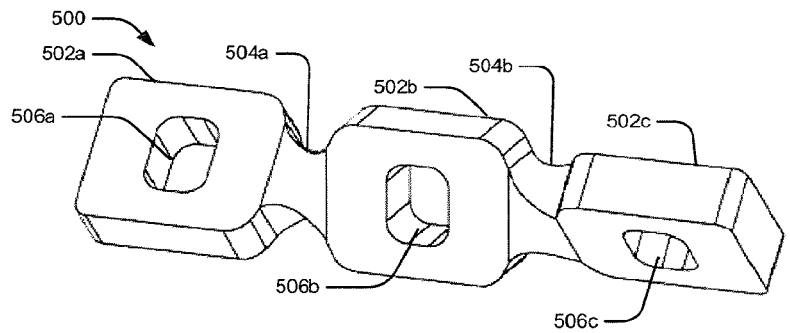
FIGS. 53A-E illustrate various views of a twisted marker having three rectangular shaped portions and two narrow portions.
Figure 53B:
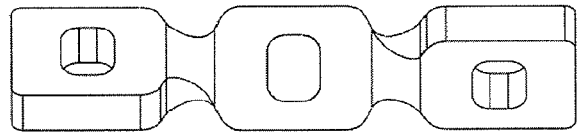
Figure 53C:
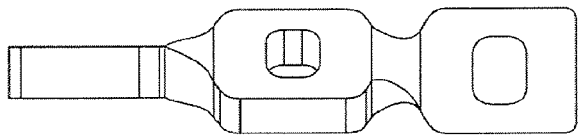
Figure 53D:
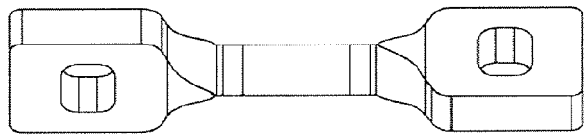
Figure 53E:
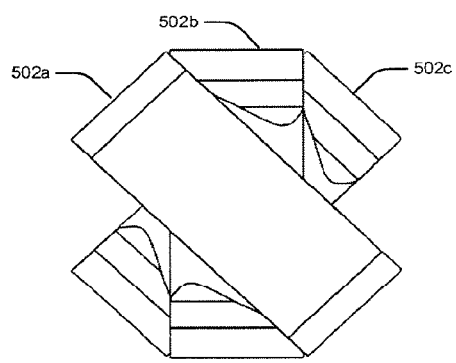

FIGS. 53A-E illustrate various views of a twisted marker 500 having three shaped portions 502 *a-c* and two narrow portions 504 *a* and *b*. The twisted marker 500 may be similar to the twisted marker 20 (FIG. 2A). Each shaped portion 502 may be shaped as a rounded rectangle. The through holes 504 may also be shaped as rounded rectangles. As illustrated in FIG. 53E, the angle between each of the shaped portions may be approximately 45°. That is, the angle between a surface of shaped portion 502*a* and a surface of shaped portion 502*b* may be a 45° angle, and the angle between a surface of shaped portion 502*b* and a surface of shaped portion 502*c* may be a 45° angle. In another aspect, the marker 500 may be twisted such that the angle between each of the shaped portions 502 may be approximately 30°.

Figure 54A:
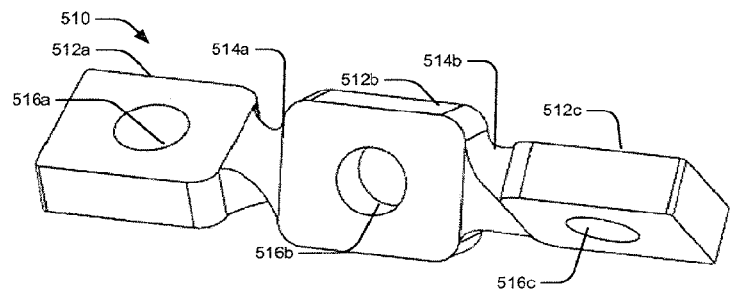
FIGS. 54A-E illustrate various views of a twisted marker having three rectangular shaped portions and two narrow portions.
Figure 54B:
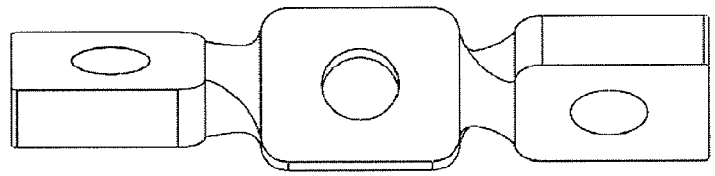
Figure 54C:
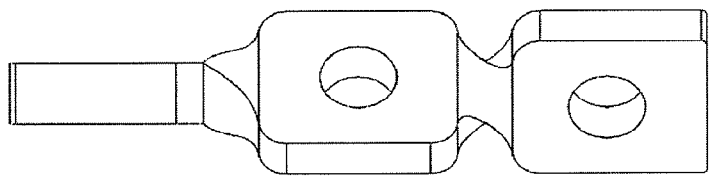
Figure 54D:
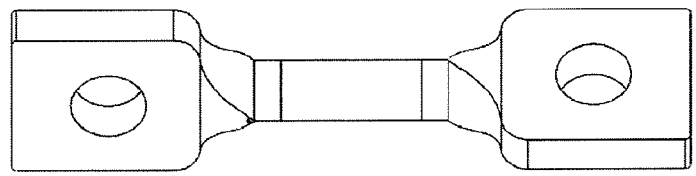
Figure 54E:
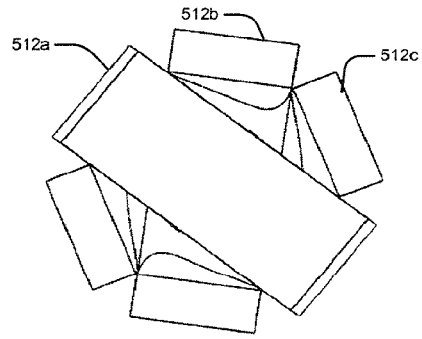
Figure 55A:
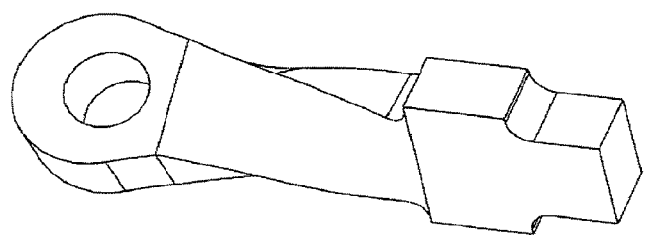
FIGS. 55A-E illustrate various views of a twisted marker having two differently shaped portions and an elongated narrow portion.
Figure 55B:
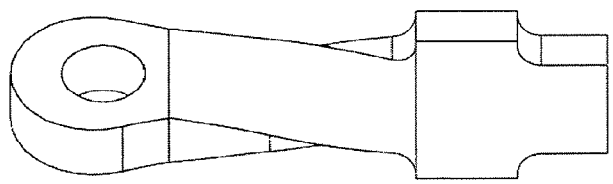
Figure 55C:
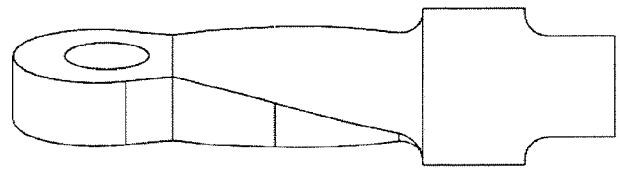
Figure 55D:
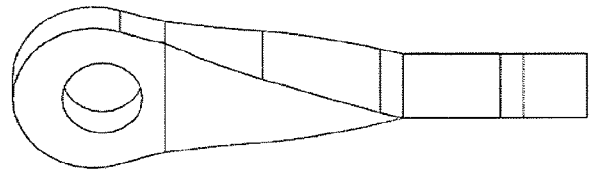
Figure 55E:
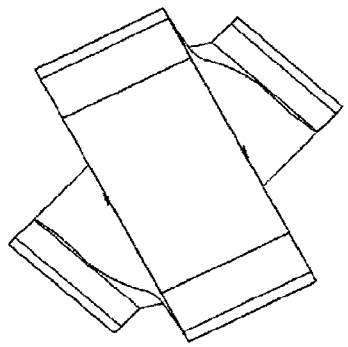
Figure 56A:
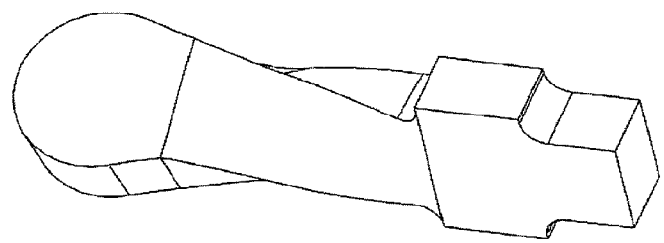
FIGS. 56A-E illustrate various views of a twisted marker without through holes.
Figure 56B:
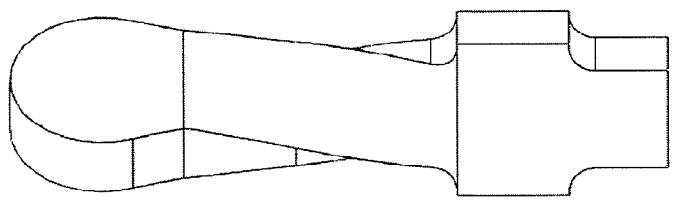
Figure 56C:
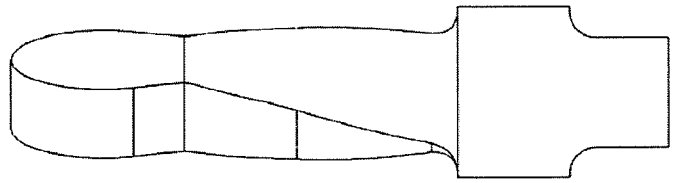
Figure 56D:
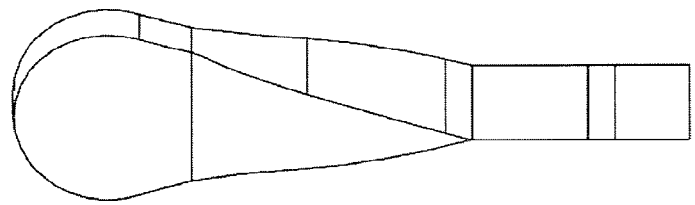
Figure 56E:
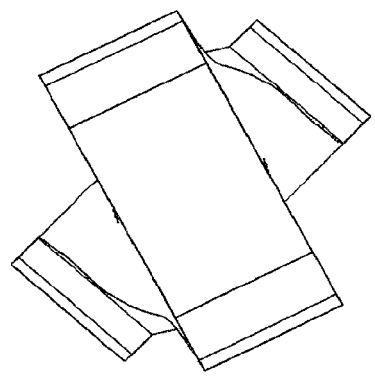
Figure 57A:
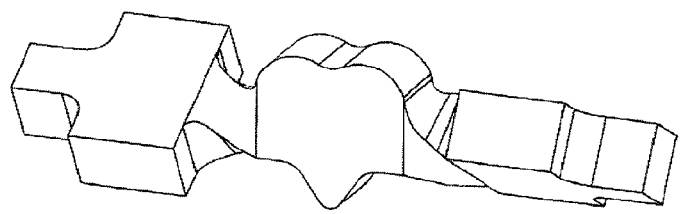
FIGS. 57A-E illustrate various views of a twisted marker having three shaped portions and two twisted portions.
Figure 57B:
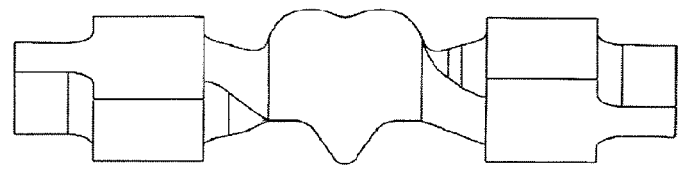
Figure 57C:
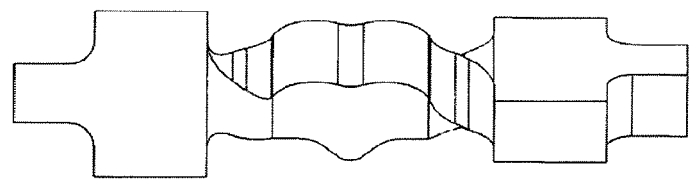
Figure 57D:
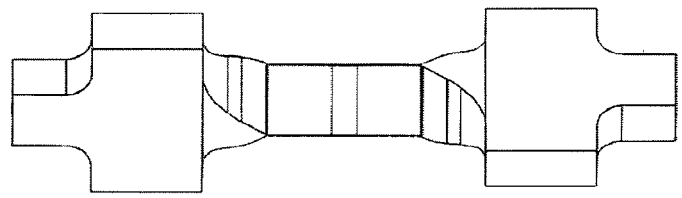
Figure 57E:
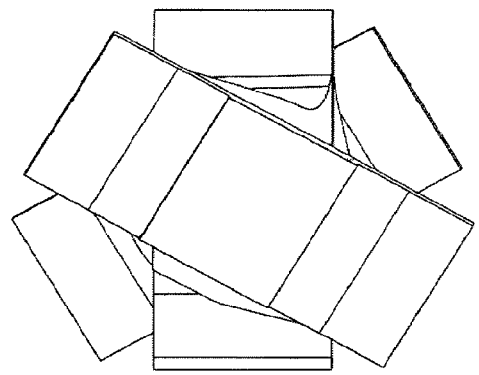

FIGS. 54A-E illustrate various views of a twisted marker 510 having three shaped portions 512 and two narrow portions 514. The twisted marker 510 may be similar to the twisted marker 20 (FIG. 2A). Each shaped portion 512 may be shaped as a rounded rectangle. The through holes 514 may be circles. As illustrated in FIG. 54E, the angle between the surfaces of each of the shaped portions may be approximately 60 degrees. That is, the angle between a surface of shaped portion 512*a* and a surface of shaped portion 512*b* may be a 60 degree angle, and the angle between a surface of shaped portion 512*b* and a surface of shaped portion 512*c* may be a 60° angle. For a marker having three shaped portions, an angle of 60 degrees may result in each of the flat surfaces being twisted to an equal angle from the other surface. That is, a surface of the shaped portion 512*a* may also be at a 60 degree angle to the surface of the shaped portion 512*c*. Such an arrangement may present a portion of a surface of a shaped portion from any angle transverse to the axis.

FIGS. 55A-E illustrate various views of a twisted marker having two differently shaped portions and an elongated narrow portion. For example, a first shaped portion may be circular. The first shaped portion may include a through hole. The second shaped portion may be cross or plus-sign shaped. The elongated narrow portion may be twisted. In an aspect, the elongated narrow portion may reduce the stress of twisting and provide strength against breakage, for example, when a bioabsorbable material surrounding the marker is compressed.

FIGS. 56A-E illustrate various views of a twisted marker similar to the marker in FIGS. 55A-E, except the twisted marker does not include a through hole.

FIGS. 57A-E illustrate various views of a twisted marker having three shaped portions and two twisted portions. The shaped portions may have different shapes. For example, as illustrated, the outer shaped portions may be shaped like a cross or plus-sign and the middle shaped portion may be shaped like a heart. The heart shape may be modified to connect to the narrow portions. Each shaped portion may also include through holes (not shown).

Figure 58A:
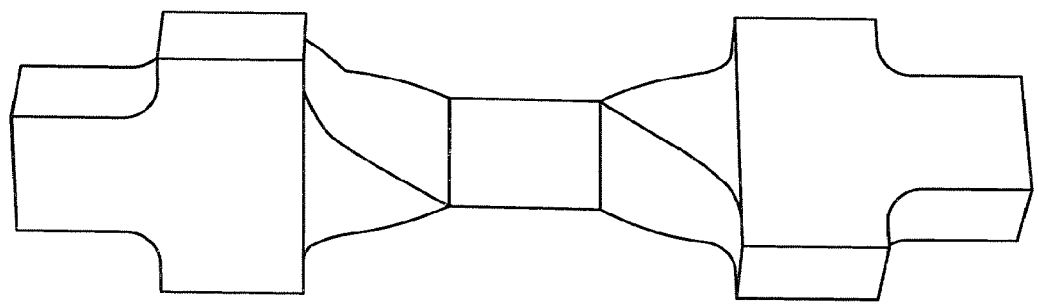
FIGS. 58A-C illustrate various views of a twisted marker having three shaped portions and two twisted portions.
Figure 58B:
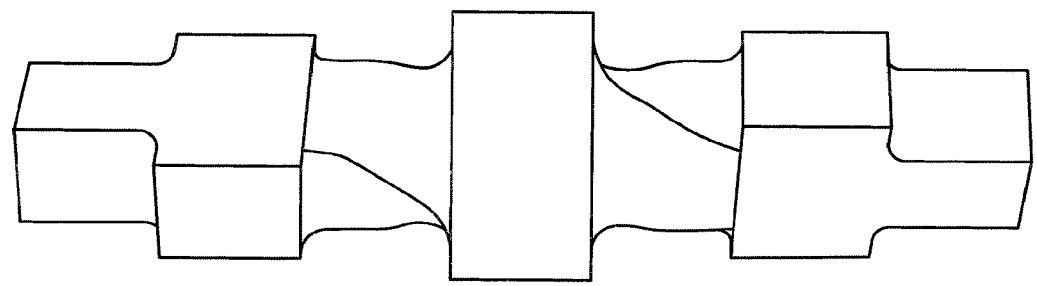
Figure 58C:
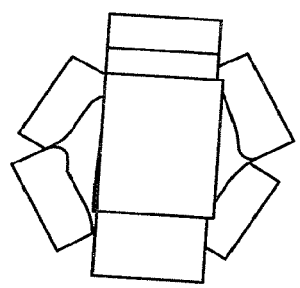

FIGS. 58A-C illustrate various views of a twisted marker having three shaped portions and two twisted portions. The outer shaped portions may be similar to those in FIG. 57, that is, shaped like a cross or plus sign. The middle shaped portion may be rectangular. The narrow portions may each be twisted to approximately 60 degrees.

Figure 59A:
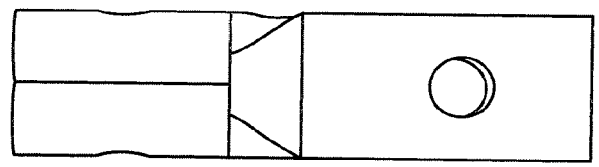
FIGS. 59A-D illustrate various views of another marker.
Figure 59B:
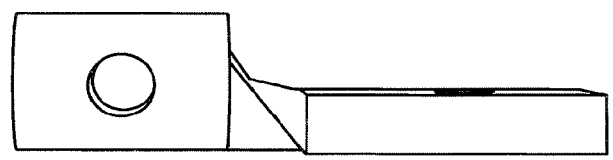
Figure 59C:
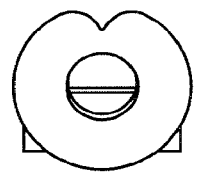
Figure 59D:
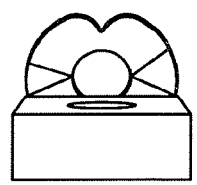

FIGS. 59A-D illustrate various views of a marker. The marker may have a shaped portion, a twisted portion, and a rolled portion. The shaped portion may be any of the shapes discussed herein. As illustrated in FIG. 59A for example, the shaped portion may be rectangular. The shaped portion may include one or more through holes. The rolled portion may be bent or rolled in one or more dimensions. In an aspect, the rolled portion may be formed from a flat shaped portion that is then rolled or bent. For example, as illustrated in FIGS. 59A-D, the rolled portion may be formed from a rectangular flat shaped portion. In an aspect, a marker blank for the marker in FIGS. 59A-D may be initially T shaped, then the top portion of the T may be rolled inward from each side. The rolled portion may also include one or more through holes. As illustrated, for example, in FIG. 59B, a through hole on each side of the rolled portion may align. The two sides of the rolled portion may meet, for example, along a center axis of the marker. The twisted portion may connect the shaped portion and the rolled portion. In an aspect, one or more sub-portions of the twisted portion may be twisted in different directions. For example, a sub-portion on one side of the twisted portion may be twisted in one direction and a sub-portion on the other side of the twisted portion may be twisted in the opposite direction. In an aspect, the marker may include a connecting portion that is not twisted, or the shaped portion may be formed contiguously with the rolled portion.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. An apparatus for marking tissue, comprising:
   (a) a cannula including a distal end and a side aperture positioned proximate the distal end;
   (b) a rod extending within the cannula, wherein the rod integrally defines a flexible deployer, wherein the flexible deployer is configured to transition from a pre-actuated state to an actuated state; and
   (c) a biopsy site marker, wherein the rod is configured to transition the flexible deployer to the actuated state to thereby expel the biopsy site marker through the side aperture, wherein the flexible deployer includes a notch proximate a distal end of the rod and lateral relative to the marker such that the notch is configured to receive the biopsy site marker.

2. The apparatus of claim 1, wherein the flexible deployer includes one or more crimps, wherein the crimps are configured to deform the flexible deployer at one or more predetermined locations.

3. The apparatus of claim 1, wherein the flexible deployer includes a plurality of crimps, wherein the crimps are configured to deform the flexible deployer at a plurality of predetermined locations.

4. The apparatus of claim 1, wherein the flexible deployer is configured to buckle in response to translation of the rod to thereby expel the biopsy site marker from the side aperture.

5. The apparatus of claim 4, wherein the flexible deployer is aligned with a longitudinal axis defined by the rod when the flexible deployer is in the pre-actuated state.

6. The apparatus of claim 4, wherein the flexible deployer is configured to transition from the pre-actuated state to the actuated state upon distal translation of the rod within the cannula.

7. The apparatus of claim 1, wherein the flexible deployer is positioned opposite of the side aperture, wherein the flexible deployer is configured to permit the biopsy site marker to be contained within the cannula when the flexible deployer is in the pre-actuated state.

8. The apparatus of claim 1, wherein the flexible deployer is integral with the rod.

9. The apparatus of claim 1, wherein the flexible deployer includes one or more crimps, wherein each crimp of the one or more crimps is configured to provide a point of weakness in the flexible deployer to thereby permit the flexible deployer to deform to a predetermined shape when compressed longitudinally by the rod.

10. A marker delivery device for use with a cannula including a side aperture, the marker delivery device comprising:
   (a) a rod configured to move within the cannula relative to the side aperture; and
   (b) a flexible deployer biased towards a flat straightened configuration extending parallel to a longitudinal axis defined by the rod, the flexible deployer being configured to deform from the straightened configuration in response to movement of the rod to expel a biopsy site marker from the side aperture of the cannula, the flexible deployer being integral with the rod and configured to releasably engage the biopsy site marker.

11. The marker delivery device of claim 10, wherein the flexible deployer is secured to the rod and extends from the rod, wherein the flexible deployer is configured to deform orthogonally relative to the longitudinal axis of the rod in response to distal translation of the rod.

12. The marker delivery device of claim 10, wherein the rod is configured to translate within the cannula to longitudinally compress the flexible deployer orthogonally relative to the longitudinal axis of the cannula and thereby expel the biopsy site marker from the side aperture.

13. The marker delivery device of claim 10, wherein the flexible deployer includes a notch configured to receive the biopsy site marker.

14. The marker delivery device of claim 13, wherein the flexible deployer further includes a plurality of crimps configured to permit deformation of the flexible deployer at a plurality of predetermined points when the flexible deployer is compressed longitudinally by the rod.

15. A method of deploying a marker, comprising:
   (a) inserting a rod of a maker delivery device into a biopsy device;
   (b) translating the rod of the marker delivery device within the biopsy device, the biopsy device including a distal end and a lateral aperture positioned proximate to the distal end;
   (c) further translating the rod of the marker delivery device into the distal end of the biopsy device to flex a flexible deployer operatively coupled to the rod and positioned proximate to the lateral aperture, wherein the translating of the rod compresses the flexible deployer between the rod and a wall defined by the distal end of the biopsy device to expel the marker out of the lateral aperture;
   (d) removing the rod of the marker delivery device from the biopsy device.

16. The method of claim 15, wherein the step of further translating the rod includes deforming the flexible deployer at one or more predetermined points of weakness in the flexible deployer.

17. The method of claim 15, wherein the step of further translating the rod includes deforming the flexible deployer at one or more notches in the flexible deployer.

18. The method of claim 15, wherein the step of further translating the rod includes deforming the flexible deployer at one or more crimps in the flexible deployer.

* * * * *